US010065969B2

(12) United States Patent
Tagami et al.

(10) Patent No.: US 10,065,969 B2
(45) Date of Patent: Sep. 4, 2018

(54) METHOD FOR PRODUCING CARBOXYLIC ACID ANHYDRIDE, METHOD FOR PRODUCING CARBOXYLIC IMIDE, AND METHOD FOR MANUFACTURING ELECTROPHOTOGRAPHIC PHOTOSENSITIVE MEMBER

(71) Applicant: CANON KABUSHIKI KAISHA, Tokyo (JP)

(72) Inventors: Kei Tagami, Yokohama (JP); Akihito Saitoh, Gotemba (JP); Kunihiko Sekido, Suntou-gun (JP); Michiyo Sekiya, Atami (JP); Masashi Nishi, Susono (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/189,827

(22) Filed: Jun. 22, 2016

(65) Prior Publication Data
US 2016/0376285 A1 Dec. 29, 2016

(30) Foreign Application Priority Data

Jun. 25, 2015 (JP) ................................. 2015-128152

(51) Int. Cl.
*G03G 5/06* (2006.01)
*C07D 493/06* (2006.01)
*C07D 471/06* (2006.01)
*C07D 307/83* (2006.01)
*C07D 487/06* (2006.01)
*G03G 5/14* (2006.01)

(52) U.S. Cl.
CPC ......... *C07D 493/06* (2013.01); *C07D 307/83* (2013.01); *C07D 471/06* (2013.01); *C07D 487/06* (2013.01); *G03G 5/142* (2013.01)

(58) Field of Classification Search
CPC ....................................................... G03G 5/06
See application file for complete search history.

(56) References Cited

U.S. PATENT DOCUMENTS

| 3,940,426 A * | 2/1976 | Itatani ..................... C07C 51/09 549/241 |
| 4,824,994 A * | 4/1989 | Takahashi ............ C07K 5/0613 560/38 |
| 8,993,710 B1 * | 3/2015 | Chuang .................. C08L 79/08 528/271 |
| 2010/0232830 A1 * | 9/2010 | Wada .................. C09B 67/0016 399/111 |
| 2011/0319620 A1 * | 12/2011 | Ishihara .................. C07C 51/56 546/13 |
| 2013/0344423 A1 * | 12/2013 | Fujii ..................... G03G 5/047 430/56 |

FOREIGN PATENT DOCUMENTS

| CN | 101405349 A | 4/2009 |
| JP | 62-59280 A | 3/1987 |
| JP | 64-50876 A | 2/1989 |
| JP | 2014-029479 A | 2/2014 |

* cited by examiner

*Primary Examiner* — Hoa V Le
(74) *Attorney, Agent, or Firm* — Canon U.S.A., Inc. IP Division

(57) ABSTRACT

A method for producing a carboxylic acid anhydride includes heating a composition containing a specific compound in a solvent to yield the carboxylic acid anhydride. The solvent is an aprotic polar solvent having a boiling point of 50° C. or more.

10 Claims, 2 Drawing Sheets

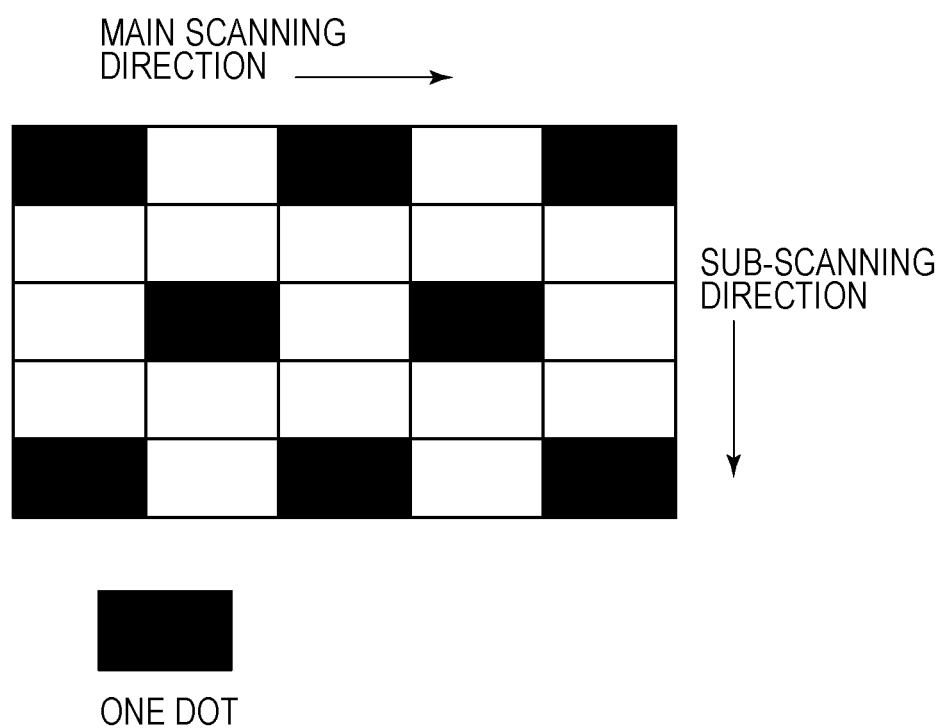

METHOD FOR PRODUCING CARBOXYLIC ACID ANHYDRIDE, METHOD FOR PRODUCING CARBOXYLIC IMIDE, AND METHOD FOR MANUFACTURING ELECTROPHOTOGRAPHIC PHOTOSENSITIVE MEMBER

BACKGROUND OF THE INVENTION

Field of the Invention

The present disclosure relates to a method for producing a carboxylic acid anhydride, a method for producing a carboxylic imide, and a method for manufacturing an electrophotographic photosensitive member.

Description of the Related Art

Carboxylic acid anhydrides such as dicarboxylic acid monoanhydrides and tetracarboxylic acid dianhydrides are widely used as a material for organic electronic devices such as electrophotographic photosensitive members, photoelectric conversion elements, and organic electric field light-emitting elements, and as a raw material or an intermediate of polyimide resins.

For example, Japanese Patent Laid-Open No. 2014-29479 discloses an electrophotographic photosensitive member used in a process cartridge or an electrophotographic apparatus, and in this disclosure, tetracarboxylic diimide produced by a reaction of a tetracarboxylic acid anhydride and an amine is used as an electron transporting material.

There have been devised processes for producing a carboxylic acid anhydride by heating a solid dicarboxylic or tetracarboxylic acid or by heating a dicarboxylic or tetracarboxylic acid in acetic anhydride. Japanese Patent Laid-Open No. 62-59280 discloses a method for dehydrating pyromellitic acid by indirectly heating pyromellitic acid with a heat medium having a temperature of 240° C. or more. Japanese Patent Laid-Open No. 1-50876 discloses a method for dehydrating biphenyltetracarboxylic acid by heating biphenyltetracarboxylic acid at 250° C. or more.

SUMMARY OF THE INVENTION

According to an aspect of the present disclosure, a method for producing a carboxylic acid anhydride including the following steps (i) to (iii):

(i) heating a composition containing a compound represented by formula (1) in a first solvent to produce a carboxylic acid anhydride represented by formula (2):

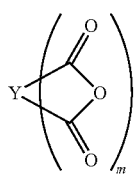
(2)

wherein formulas (1) and (2), Y represents a divalent to hexavalent organic group, n represents an integer of 2 to 6, and m represents an integer of 1 to 3;

(ii) heating a composition containing at least one compound selected from the group consisting of compounds represented by formula (3) and compounds represented by formula (4) in a second solvent to prepare a carboxylic acid anhydride represented by formula (5):

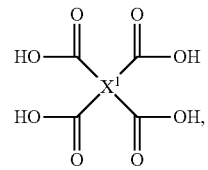
(3)

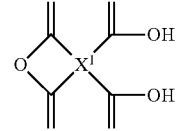
(4)

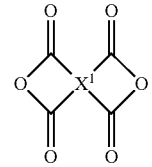
(5)

wherein in formulas (3) to (5), $X^1$ represents a residue being a tetracarboxylic acid from which four carboxy groups are removed; and (iii) heating a composition containing a compound represented by formula (6) in a third solvent to produce a carboxylic acid anhydride represented by formula (7):

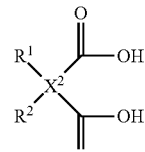
(6)

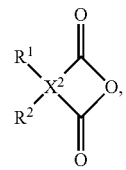
(7)

wherein in formulas (6) and (7), $R^1$ represents an atom or group selected from the group consisting of a hydrogen atom, alkyl groups, halogen atoms, and a carboxy group, $R^2$ represents an atom or a group selected from the group consisting of a hydrogen atom, alkyl groups, and halogen atoms, and $X^2$ represents a residue of dicarboxylic acid from which two carboxy groups are removed.

In these steps, the solvent contains an aprotic polar solvent having a boiling point of 50° C. or more.

According to another aspect of the present disclosure, a method for producing a carboxylic imide is provided. In this method, a carboxylic acid anhydride produced by the above method is used.

According to still another aspect of the present disclosure, a method for manufacturing an electrophotographic photosensitive member including a support member, an undercoat layer over the support member, and a photosensitive layer on the undercoat layer is provided. The method includes preparing an undercoat layer-forming coating liquid containing a carboxylic imide produced by the foregoing method, and forming the undercoat layer by applying the undercoat layer-forming coating liquid to form a coating film and drying the coating film.

Further features of the present invention will become apparent from the following description of exemplary embodiments with reference to the attached drawings.

BRIEF DESCRIPTION OF THE DRAWINGS

FIG. 3 is an illustrative representation of a halftone image in a dot pattern like chess knight (Shogi keima) movement.

DESCRIPTION OF THE EMBODIMENTS

Figure 1:
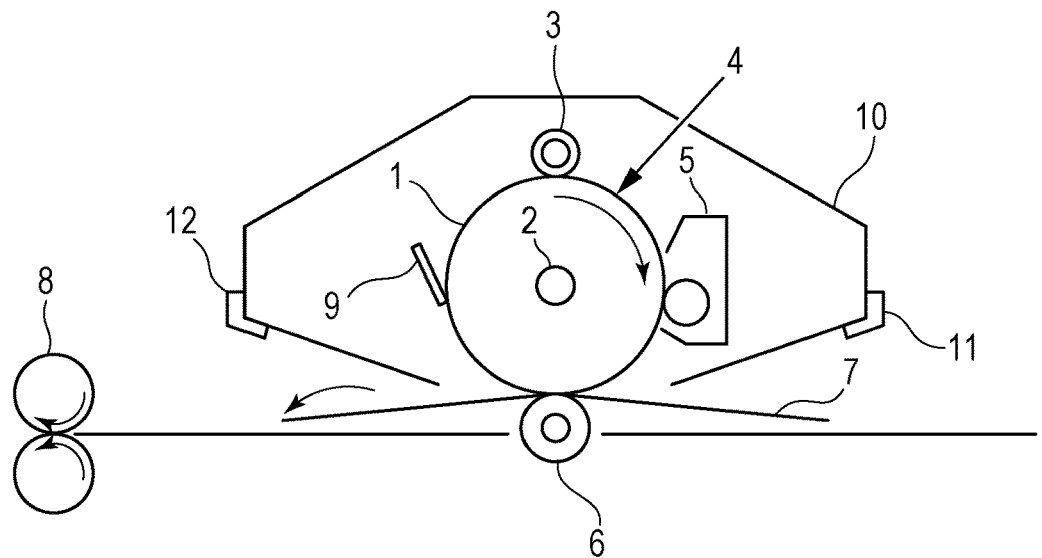
FIG. 1 is a schematic view of the structure of an electrophotographic apparatus provided with a process cartridge including an electrophotographic photosensitive member.

The processes disclosed in the above-cited Japanese Patent Laid-Open Nos. 62-59280 and 1-50876 of producing a carboxylic acid anhydride by heating a solid dicarboxylic or tetracarboxylic acid are performed at a high temperature and accordingly require a large amount of energy for heating. When a carboxylic acid anhydride is produced at a high temperature, the resulting product may be colored in some cases, or a by-product can be produced. Also, when an acid such as acetic anhydride is used, acid-resistant equipment and disposal of the acid are required.

Accordingly, the present disclosure provides novel methods for producing a carboxylic acid anhydride and for producing a carboxylic imide. Also, the present disclosure is directed to providing a method for manufacturing an electrophotographic photosensitive member that can from high-quality images.

The present inventors have devised processes for producing a carboxylic acid anhydride at low temperature or without using an acid solvent through their intensive research.

One of the processes uses a composition containing a compound represented by the following formula (1):

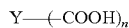

(1)

In formula (1), Y represents a divalent to hexavalent organic group, and n represents an integer of 2 to 6.

The composition is heated in a solvent, and thus a carboxylic acid anhydride represented by the following formula (2) is produced:

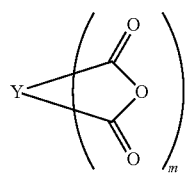

(2)

In formula (2), Y represents a divalent to hexavalent organic group, and m represents an integer of 1 to 3.

The solvent contains an aprotic polar solvent having a boiling point of 50° C. or more.

An alternative process of the disclosure for producing a carboxylic acid anhydride uses a composition containing at least one compound selected from the group consisting of the compounds expressed by formula (3) and the compounds represented by formula (4):

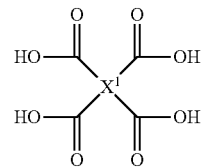

(3)

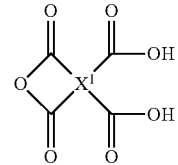

(4)

The composition is heated in a solvent, and thus a carboxylic acid anhydride (tetracarboxylic acid dianhydride) represented by formula (5) is produced:

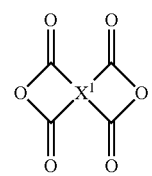

(5)

The solvent contains an aprotic polar solvent having a boiling point of 50° C. or more.

In formulas (3) to (5), $X^1$ represents a residue of a tetracarboxylic acid, formed by removing the four carboxy groups from the tetracarboxylic acid.

In another embodiment of the present disclosure, a process for producing a carboxylic acid anhydride uses a composition containing a compound represented by the following formula (6):

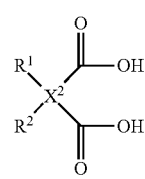

(6)

The composition is heated in a solvent, and thus a carboxylic acid anhydride (carboxylic acid monoanhydride) represented by formula (7) is produced:

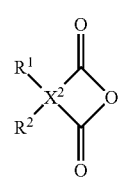

(7)

The solvent contains an aprotic polar solvent having a boiling point of 50° C. or more.

In formulas (6) and (7), $R^1$ represents an atom or a group selected from the group consisting of a hydrogen atom, alkyl groups, halogen atoms, and a carboxy group. $R^2$ represents an atom or a group selected from the group consisting of a hydrogen atom, alkyl groups, and halogen atoms. $X^2$ represents a residue of a dicarboxylic acid, formed removing the two carboxy groups from the dicarboxylic acid.

According to the method of the present disclosure, a carboxylic acid anhydride can be produced at low temperature or without using an acid solvent. The present inventors assume that the reason why carboxylic acid anhydride is produced at low temperature or without using an acid solvent is as bellow.

In the method of the present disclosure, an aprotic polar solvent is used as the solvent of the composition containing a compound represented by formula (1). It is assumed the aprotic polar solvent weakens the hydrogen bonds between the carboxy groups in the molecule of the compound represented by formula (1) and thereby reduces the energy required for dehydration. The inventors thought that the dehydration reaction thus proceeds to produce a carboxylic acid anhydride even at low temperature or without using an acid solvent. Although low-temperature reactions tend to take a long time, the dehydration reaction can be performed at a low temperature for a relatively short time because the boiling point of the aprotic polar solvent is 50° C. or more (the heating temperature can be 50° C. or more).

Raw Materials for Producing Carboxylic Acid Anhydride

The raw material composition for producing the carboxylic acid anhydride according to an embodiment of the present disclosure contains at least one compound selected from the group consisting of:

(I) compounds (polyvalent carboxylic acid) represented by any one of formulas (1), (3), and (6); and (II) compounds (carboxylic acid anhydride having carboxy groups) represented by formula (4).

For example, the composition may contain a dicarboxylic acid and a tricarboxylic acid, or contain a tetracarboxylic acid and a tetracarboxylic acid monoanhydride. The composition may further contain a carboxylic acid anhydride not containing a carboxy group.

Examples of the carboxylic acid represented by formula (1) include hexacarboxylic acids, pentacarboxylic acids, tetracarboxylic acid, tricarboxylic acids, and dicarboxylic acids. The hexacarboxylic acid may be benzenehexacarboxylic acid. The pentacarboxylic acid may be benzenepentacarboxylic acid.

In formulas (1) and (2), the organic group Y may further contain an atom or a functional group selected from the group consisting of a hydrogen atom, halogen atoms, a cyano group, a nitro group, a carboxylate ester group, and substituted or unsubstituted alkyl groups.

The compound (tetracarboxylic acid) represented by formula (3) may be an aromatic tetracarboxylic acid. Examples of the aromatic tetracarboxylic acid include 1,2,3,4-benzenetetracarboxylic acid, 1,2,4,5-benzenetetracarboxylic acid, 2,2',3,3'-biphenyltetracarboxylic acid, 3,3',4,4'-biphenyltetracarboxylic acid, 2,3,3',4'-biphenyltetracarboxylic acid, 3,3',4,4'-p-terphenyltetracarboxylic acid, 2,2',3,3'-p-terphenyltetracarboxylic acid, 2,3,3',4'-p-terphenyltetracarboxylic acid, 1,2,4,5-naphthalenetetracarboxylic acid, 1,2,5,6-naphthalenetetracarboxylic acid, 1,4,5,8-naphthalenetetracarboxylic acid, 2,3,6,7-naphthalenetetracarboxylic acid, 2,3,6,7-anthracenetetracarboxylic acid, and 3,4,9,10-perylenetetracarboxylic acid.

The compound represented by formula (4) may be an aromatic tetracarboxylic acid monoanhydride. Examples of the aromatic tetracarboxylic acid monoanhydride include 1,2,3,4-benzenetetracarboxylic acid 1,2-monoanhydride, 1,2,4,5-benzenetetracarboxylic acid 1,2-monoanhydride, 2,2',3,3'-biphenyltetracarboxylic acid 2,3-monoanhydride, 3,3',4,4'-biphenyltetracarboxylic acid 3,4-monoanhydride, 2,3,3',4'-biphenyltetracarboxylic acid 2,3-monoanhydride, 3,3',4,4'-p-terphenyltetracarboxylic acid 3,4-monoanhydride, 2,2',3,3'-p-terphenyltetracarboxylic acid 2,3-monoanhydride, 2,3,3',4'-p-terphenyltetracarboxylic acid 2,3-monoanhydride, 1,2,4,5-naphthalenetetracarboxylic acid 1,2-monoanhydride, 1,2,5,6-naphthalenetetracarboxylic acid 1,2-monoanhydride, 1,4,5,8-naphthalenetetracarboxylic acid 1,8-monoanhydride, 2,3,6,7-naphthalenetetracarboxylic acid 2,3-monoanhydride, 2,3,6,7-anthracenetetracarboxylic acid 2,3-monoanhydride, and 3,4,9,10-perylenetetracarboxylic acid 3,4-monoanhydride.

The compound represented by formula (5) may be an aromatic tetracarboxylic acid dianhydride. Examples of the aromatic tetracarboxylic acid dianhydride include 1,2,3,4-benzenetetracarboxylic acid dianhydride, 1,2,4,5-benzenetetracarboxylic acid dianhydride, 2,2',3,3'-biphenyltetracarboxylic acid dianhydride, 3,3',4,4'-biphenyltetracarboxylic acid dianhydride, 2,3,3',4'-biphenyltetracarboxylic acid dianhydride, 3,3',4,4'-p-terphenyltetracarboxylic acid dianhydride, 2,2',3,3'-p-terphenyltetracarboxylic acid dianhydride, 2,3,3',4'-p-terphenyltetracarboxylic acid dianhydride, 1,2,4,5-naphthalenetetracarboxylic acid dianhydride, 1,2,5,6-naphthalenetetracarboxylic acid dianhydride, 1,4,5,8-naphthalenetetracarboxylic acid dianhydride, 2,3,6,7-naphthalenetetracarboxylic acid dianhydride, 2,3,6,7-anthracenetetracarboxylic acid dianhydride, and 3,4,9,10-perylenetetracarboxylic acid dianhydride.

The compound represented by formula (6) may be an aromatic dicarboxylic or tricarboxylic acid. Examples of the aromatic dicarboxylic acid include 1,8-naphthalenedicarboxylic acid, 2,3-naphthalenedicarboxylic acid, 4-methylphthalic acid, 4-bromophthalic acid, 4,5-dichlorophthalic acid, and 4-trifluoromethylphthalic acid. Examples of the aromatic tricarboxylic acid include trimellitic acid and 1,2,3-benzenetricarboxylic acid.

Advantageously, Y in formulas (1) and (2), $X^1$ in formulas (3) to (5), and $X^2$ in formulas (6) and (7) are each a group represented by any one of the following formulas (10), (11) and (12). The group represented by formula (12) is more advantageous.

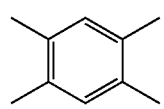

(10)

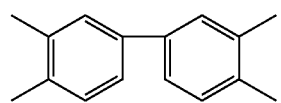

(11)

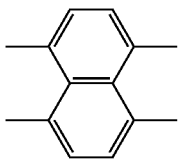

(12)

When Y, $X^1$, and $X^2$ are each a group represented by any one of formulas (10) to (12), the energy required for the dehydration of carboxy groups in the molecule can efficiently reduced. The present inventors assume that this is because the groups represented by these formulas make the compounds of formula (1), (3), (4), or (6) form a molecular structure in which the carboxy groups are likely to cause a dehydration reaction.

Aprotic Polar Solvent

In the method of the present disclosure, the raw material composition is heated in an aprotic polar solvent. An aprotic solvent is a solvent that does not have a dissociative hydrogen atom. Also, an aprotic polar solvent is an aprotic solvent having a large dipole moment and a high dielectric constant. Two or more aprotic polar solvents may be used in combination without limitation to the use of a single aprotic polar solvent. If two or more aprotic polar solvents are used in combination, the "boiling point of the aprotic polar solvent" mentioned herein refers to the lowest of the boiling points of the aprotic polar solvents. Aprotic polar solvents include fatty acid esters, amides, sulfoxides, and ketones.

Examples of the aprotic polar solvent will be cited below, but it is not limited to the cited solvents.

Exemplary fatty acid esters include methyl acetate, ethyl acetate, propyl acetate, isopropyl acetate, butyl acetate, pentyl acetate, methyl propionate, methyl valerate, ethyl valerate, methyl hexanoate, ethyl hexanoate, methyl heptanoate, ethyl heptanoate, methyl n-octanoate, and ethyl n-octanoate.

Amides may be represented by the following formula (8):

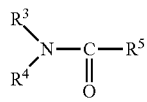

(8)

In formula (8), $R^3$ and $R^4$ each represent an alkyl group, and $R^5$ represents a hydrogen atom or an alkyl group.

More specifically, examples of the compound represented by formula (8) include N,N-dimethylformamide, N,N-diethylformamide, and N,N-dimethylacetamide.

Sulfoxides may be represented by the following formula (9):

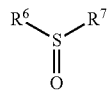

(9)

In formula (9), $R^6$ and $R^7$ each represent an alkyl group.

More specifically, the compound represented by formula (9) may be dimethyl sulfoxide.

Exemplary ketones include acetone, methyl ethyl ketone, methyl isobutyl ketone, isopropyl methyl ketone, diisopropyl ketone, tert-butyl methyl ketone, 2-pentanone, 3-pentanone, 2-heptanone, 4-heptanone, cyclobutanone, cyclopentanone, and cyclohexanone.

The alkyl groups represented by $R^3$ to $R^7$ in the compounds of formula (8) and (9) include methyl, ethyl, propyl, isopropyl, butyl, isobutyl, sec-butyl, and tert-butyl.

Solvents Other Than Aprotic Polar Solvent

The solvent may further contain at least one solvent selected from the group consisting of hydrocarbons, halogen-containing solvents, and ethers, in addition to the aprotic polar solvent from the viewpoint of reducing water, which is hinder the dehydration reaction, from the reaction liquid to promote the reaction. These additional solvents may be used singly or in combination. The amount of the additional solvent is not particularly limited as long as a carboxylic acid anhydride can be produced. For example, it may be 0.5 to 20 times, such as 1 to 10 times, relative to the amount of the aprotic polar solvent.

Hydrocarbons include aromatic hydrocarbons and aliphatic hydrocarbons. The aliphatic hydrocarbon may be a chain hydrocarbon or an alicyclic hydrocarbon.

Examples of the aromatic hydrocarbon include toluene, o-xylene, m-xylene, p-xylene, cumene, mesitylene, p-cymene, 1,2,4,5-tetramethylbenzene, and tert-butylbenzene.

Examples of the chain aliphatic hydrocarbon include heptane, hexane, and octane.

Examples of the alicyclic hydrocarbon include cyclohexane, methylcyclohexane, ethylcyclohexane, cycloheptane, and cyclooctane.

Examples of the halogen-containing solvent include chloroform, chlorobenzene, bromobenzene, 1,2-dichlorobenzene, 1,3-dichlorobenzene, and 1,2,4-trichlorobenzene.

Examples of the ether include dipropyl ether, diisopropyl ether, and dibutyl ether.

The reaction in the method of the present disclosure is performed at a temperature within the range in which the carboxylic acid anhydride can be produced, and the reaction temperature may be, but is not limited to, 50° C. to 180° C., preferably 50° C. to 150° C., such as 50° C. to 130° C. When the reaction temperature is in such a range, the reaction can be performed under industrially advantageous conditions where the resulting carboxylic acid anhydride is unlikely to be degraded.

The amount of the solvent used in the method of the present disclosure is not particularly limited as long as a carboxylic acid anhydride can be produced, and the proportion of the solvent may be 1% to 50% by mass relative to the mass of the raw material composition. Advantageously, it is 1% to 30% by mass, such as 1% to 20% by mass.

The reaction time is within a range in which the carboxylic acid anhydride can be produced, and it may be, but is not limited to, 0.1 to 30 hours, such as 0.1 to 20 hours.

The reaction may be performed under normal pressure, increased pressure, or reduced pressure, and advantageously in an atmosphere of an inert gas such as nitrogen.

The composition used in the method of the present disclosure, containing at least one selected from the group consisting of polyvalent carboxylic acids and carboxy group-containing carboxylic acid anhydrides can be synthesized by a known process, and is commercially available from, for example, Tokyo Chemical Industry, Sigma-Aldrich, or Wako Pure Chemical Industries.

Process for Producing Carboxylic Imide

The carboxylic acid anhydride produced by the method of the present disclosure can be used for producing a carboxylic imide by condensation with an amine. A process for synthesizing a carboxylic imide is disclosed in, for example, Japanese Patent Laid-Open No. 2007-108670 and NIHON GAZO GAKKAISHI (Journal of the Imaging Society of Japan, in Japanese) 45 (6), 521-525 (2006). Two or more amines may be used for the condensation reaction without limitation to the use of a single amine. The use of the carboxylic acid anhydride for synthesis of a carboxylic imide reduces the amount of by-product.

Carboxylic imides can be used as a material for organic electronic devices such as photoelectric conversion elements and organic electric-field light-emitting elements, and used in electrophotographic photosensitive members. In particular, from the viewpoint of producing a tetracarboxylic diimide, which is industrially useful, the carboxylic acid anhydride is desirably a tetracarboxylic acid anhydride.

Electrophotographic Photosensitive Member and Method for Manufacturing the Same

In general, an electrophotographic photosensitive member includes a support member and a photosensitive layer on the support member. A negatively chargeable electrophotographic photosensitive member includes a photosensitive layer containing a charge generating material and a hole transporting material. The photosensitive layer containing a charge generating material and a hole transporting material may have a multilayer structure including a charge generating layer containing the charge generating material and a hole transport layer containing the hole transporting material that are formed in that order from the support member, or may be defined by a single layer containing the charge generating material and the hole transporting material together.

If the photosensitive layer (charge generating layer) is directly disposed on the support member, the photosensitive layer may peel from the support member, or a defect (a shape defect such as a flaw or a material defect such as impurities) in or on the surface of the support member can cause image defects in the form of, for example, black spots or white spots.

In order to solve these problems, many of the photosensitive members have what is called an undercoat layer (may be called intermediate layer) between the photosensitive layer and the support member.

The carboxylic imide may be contained in any of the undercoat layer, the photosensitive layer, the charge generating layer, and the hole transport layer, and advantageously in the undercoat layer.

The method for manufacturing the electrophotographic photosensitive member includes preparing an undercoat layer-forming coating liquid, and forming the undercoat layer by forming a coating film of the undercoat layer-forming coating liquid and drying the coating film. The carboxylic imide is contained in the undercoat layer-forming coating liquid. The electrophotographic photosensitive member including the undercoat layer, manufactured by the method of the present disclosure can provide good electrophotographic properties and can particularly suppress positive ghost. Advantageously, the carboxylic imide used in the method for manufacturing the electrophotographic photosensitive member according to the present disclosure is a tetracarboxylic diimide.

Support Member

The support member is desirably electrically conductive (electroconductive support member), and may be made of a metal, such as aluminum, nickel, copper, gold, or iron, or an alloy thereof. Alternatively, an insulating support member made of, for example, polyester, polycarbonate, polyimide, or glass may be coated with a metal thin film made of, for example, aluminum, silver, or gold or any other electroconductive thin film made of, for example, indium oxide or tin oxide.

The support member may be subjected to surface treatment to improve the electrical properties and suppress interference fringes, which is likely to occur when being irradiated with coherent light such as semiconductor laser light. Such surface treatment may be performed by wet honing, blast, cutting, or electrochemical operation such as anodization. The support member may be provided with an electroconductive layer thereon. The electroconductive layer can be formed by applying a coating liquid for forming the electroconductive layer containing electroconductive particles dispersed in a resin onto the surface of the support member, and drying the coating film on the support member. Examples of the electroconductive particles include carbon black, acetylene black, powder of metal such as aluminum, nickel, iron, Nichrome, copper, zinc or silver, and powder of a metal oxide such as electroconductive tin oxide or ITO.

The resin used in the electroconductive layer may be a polyester resin, a polycarbonate resin, a polyvinyl butyral resin, an acrylic resin, a silicone resin, an epoxy resin, a melamine resin, a urethane resin, a phenol resin, or an alkyd resin.

The solvent used in the coating liquid for the electroconductive layer may be an ether-based solvent, an alcohol-based solvent, a ketone-based solvent, or an aromatic hydrocarbon. The electroconductive layer may have a thickness in the range of 0.2 μm to 40 μm.

Undercoat Layer

The undercoat layer is disposed between the charge generating layer and the support member.

In the present disclosure, the undercoat layer contains a carboxylic imide and is formed over the support member. The undercoat layer can be formed by applying an undercoat layer-forming coating liquid, and drying the coating.

The undercoat layer may further contain a resin, a crosslinking agent, organic particles, inorganic particles, a leveling agent, or other additives in addition to the above-described carboxylic imide, from the viewpoint of facilitating the formation of the undercoat layer and improving the electrical properties of the undercoat layer. The content of these additives in the undercoat layer is desirably less than 50% by mass, more desirably less than 20% by mass, relative to the total mass of the undercoat layer.

Crosslinking Agent

Any crosslinking agent can be added to the undercoat layer as long as it can be involved in crosslinking of the material of the undercoat layer. Examples of the crosslinking agent include, but are not limited to, the isocyanate compounds and amine compounds cited below. A plurality of crosslinking agents may be used in combination.

Advantageously, the isocyanate compound has two or more isocyanate groups or blocked isocyanate groups. Examples of such an isocyanate compound include benzene triisocyanate, methylbenzene triisocyanate, triphenylmethane triisocyanate, and lysine triisocyanate; isocyanurate-modified, biuret-modified, or allophanate-modified compounds of diisocyanates, such as tolylene diisocyanate, hexamethylene diisocyanate, dicyclohexylmethane diisocyanate, naphthalene diisocyanate, diphenylmethane diisocyanate, isophorone diisocyanate, xylylene diisocyanate, 2,2,4-trimethylhexamethylene diisocyanate, methyl-2,6-diisocyanate hexanoate, and norbornane diisocyanate; and trimethylolpropane adducts or pentaerythritol adducts of these diisocyanates. Isocyanurate-modified compounds and adducts are particularly advantageous.

Exemplary commercially available isocyanate compounds that can be used as the crosslinking agent include isocyanate-based crosslinking agents, such as DURANATE series MFK-60B and SBA-70B produced by Asahi Kasei and DESMODUR series BL 3175 and BL 3475 produced by Sumika Bayer Urethane; amino-based crosslinking agents, such as U-VAN series 20SE60 and 220 produced by Mitsui Chemicals and Super Beckamine series L-125-60 and G-821-60 produced by DIC; and acrylic crosslinking agents, such as FANCRYL series FA-129AS and FA-731A produced by Hitachi Chemical.

Advantageously, the amine compound used as the crosslinking agent has two or more N-methylol groups or alkyletherified N-methylol groups. Examples of such an amine compound include methylolated melamines, methylolated guanamines, methylolated urea derivatives, methylolated ethylene urea derivatives, methylolated glycolurils, compounds having an alkyletherified methylol site, and derivatives of these compounds.

Exemplary commercially available amine compounds that can be used as the crosslinking agent include Super Melami No. 90 (produced by NOF); Super Beckamine (R) series TD-139-60, L-105-60, L-127-60, L-110-60, J-820-60, G-821-60, L-148-55, 13-535, L-145-60, and TD-126 (each produced by DIC); U-VAN 2020 (produced by Mitsui Chemicals); Sumitex Resin M-3 (produced by Sumitomo Chemical); and NIKALAC series MW-30, MW-390, MX-750LM, BL-60, BX-4000, MX-280, MX-270, and MX-290 (produced by Nippon Carbide).

Resin

Examples of the resin that can be added to the undercoat layer include, but are not limited to, polyether-polyol resin, polyester-polyol resin, polyacrylic polyol resin, polyvinyl alcohol resin, polyvinyl acetal resin, polyamide resin, carboxy-containing resin, polyamine resin, and polythiol resin. Some of these resins may be used in combination.

An undercoat layer-forming coating liquid containing the carboxylic imide and the crosslinking agent may further contain a resin having a polymerizable functional group for curing the coating liquid. The cured coating liquid prevents the carboxylic imide from being degraded.

Exemplary commercially available resins having a polymerizable functional group include polyether-polyol resin, such as AQD-457 and AQD-473 (produced by Nippon Polyurethane Industry) and SANNIX GP series GP-400 and GP-700 (produced by Sanyo Chemical Industries); polyester-polyol resin, such as Phthalkyd W 2343 (produced by Hitachi Chemical), WATERSOL series S-118 and CD-520 (produced by DIC), and HARIDIP WH-1188 (produced by Harima Chemicals); polyacrylic polyol resin, such as BURNOCK series WE-300 and WE-304 (produced by DIC); polyvinyl alcohol resin, such as POVAL PVA-203 (produced by Kuraray); polyvinyl acetal resin, such as BX-1, BM-1, KS-1, and KS-5 (produced by Sekisui Chemical); polyamide resin, such as Toresin FS-350 (produced by Nagase Chemtex); carboxy-containing resin, such as AQUALIC (produced by Nippon Shokubai) and FINELEX SG 2000 (produced by Namariichi); polyamine resin, such as LUCKAMIDE (produced by DIC); and polythiol resin, such as QE-340M (produced by Toray).

Photosensitive Layer

The undercoat layer is provided thereon with a photosensitive layer containing a charge generating material and a hole transporting material.

The photosensitive layer may have a multilayer structure including a charge generating layer containing the charge generating material and a hole transport layer containing the hole transporting material that are formed in that order from the support member, or may be defined by a single layer containing the charge generating material and the hole transporting material together. The charge generating layer and the hole transport layer each may include a plurality of layers.

Examples of the charge generating material include azo pigments, such as monoazo pigments, bisazo pigments, and triazo pigments; perylene pigments, such as perylenecarboxylic acid anhydride and perylenecarboxylic imide; quinone pigments, such as anthraquinone derivatives, anthanthrone derivatives, dibenzpyrenequinone derivatives, pyranthrone derivatives, violanthrone derivatives, and isoviolanthrone derivatives; indigoid pigments, such as indigo derivatives and thioindigo derivatives; phthalocyanine pigments, such as metal phthalocyanines and non-metal phthalocyanines; and perinone pigments, such as bisbenzimidazole derivatives. Among these, azo pigments and phthalocyanine pigments are advantageous. Advantageous phthalocyanine pigments include oxytitanium phthalocyanine, chlorogallium phthalocyanine, and hydroxygallium phthalocyanine.

If the photosensitive layer has a multilayer structure, the binder resin used in the charge generating layer can be selected from among polymers or copolymers of vinyl compounds, such as styrene, vinyl acetate, vinyl chloride, acrylic acid esters, methacrylic acid esters, vinylidene fluoride, and trifluoroethylene; and polyvinyl alcohol, polyvinyl acetal, polycarbonate, polyester, polysulfone, polyphenylene oxide, polyurethane, cellulose resin, phenol resin, melamine resin, silicone resin, and epoxy resin. Among these, polyester, polycarbonate, and polyvinyl acetal are advantageous. Polyvinyl acetal is particularly advantageous.

In the charge generating layer, the mass ratio of the charge generating material to the binder resin (mass of the charge generating material/mass of the binder resin) may be in the range of 10/1 to 1/10, such as 5/1 to 1/5. The thickness of the charge generating layer may be in the range of 0.05 μm to 5 μm.

Examples of the hole transporting material in the hole transport layer include polycyclic aromatic compounds, heterocyclic compounds, hydrazone compounds, styryl compounds, benzidine compounds, triarylamine compounds, and triphenylamine. Alternatively, the charge transport material may be a polymer having a group derived from these compounds in the main chain or a side chain.

If the photosensitive layer has a multilayer structure, the binder resin used in the hole transport layer can be selected from among polyester, polycarbonate, polymethacrylate, polyarylate, polysulfone, and polystyrene. Among these, polycarbonate and polyarylate are advantageous. The weight average molecular weight (Mw) of the binder resin may be in the range of 10,000 to 300,000.

In the hole transport layer, the mass ratio of the hole transporting material to the binder resin (mass of the hole transporting material/mass of the binder resin) may be in the range of 10/5 to 3/10, such as 10/8 to 6/10.

An additional layer may be formed between the support member and the undercoat layer or between the undercoat layer and the photosensitive layer. The additional layer may be an electroconductive layer formed by dispersing electroconductive particles of a metal oxide or carbon black in a resin, or a second undercoat layer not containing a resin having a polymerizable group.

The hole transport layer of the photosensitive member may be provided thereon with a protective layer (surface protection layer) containing a binder resin and electroconductive particles or a hole transporting material. The protective layer may further contain an additive, such as a lubricant. The binder resin in the protective layer may have electrical conductivity or hole transportability. In this instance, the protective layer need not contain electroconductive particles or hole transporting material in addition to the binder resin. The binder resin in the protective layer may be thermoplastic, or may be a resin curable by heat, light, or radiation (e.g. electron beam).

Formation of Layers

Each layer of the electrophotographic photosensitive member, such as the undercoat layer, the charge generating layer, and the hole transport layer, may be formed by applying a coating liquid prepared by dissolving or dispersing the materials of the layer in a solvent so as to form a coating film of the coating liquid. The coating film is desirably dried and/or cured. The coating liquid may be applied by dipping (dip coating), spray coating, curtain coating, or spin coating. From the viewpoint of efficiency and productivity, dip coating is advantageous.

Process Cartridge and Electrophotographic Apparatus

FIG. 1 is a schematic view of the structure of an electrophotographic apparatus provided with a process cartridge including an electrophotographic photosensitive member.

The electrophotographic photosensitive member 1 of the electrophotographic apparatus shown in FIG. 1 is driven for rotation on a rotation shaft 2 in the direction indicated by the corresponding arrow at a predetermined peripheral speed. The surface (periphery) of the electrophotographic photosensitive member 1 is uniformly charged to a predetermined positive or negative potential with a charging device 3 (for example, a contact-type primary charging device or a non-contact-type primary charging device) for rotation. Then, the uniformly charged surface or periphery is exposed to light (image exposure light) 4 from an exposure device (image exposure device, not shown), such as a slit exposure device or a laser beam scanning exposure device. Thus electrostatic latent images corresponding to desired images are formed one after another on the surface of the electrophotographic photosensitive member 1.

The electrostatic latent images formed on the surface of the electrophotographic photosensitive member 1 are then developed into toner images with the toner contained in the developing device 5 (such as a contact-type developing device or a non-contact type developing device). The resulting toner images are transferred to a transfer medium 7 (such as paper) one after another with a transfer device 6 (such as a transfer charger). The transfer medium 7 is fed to a portion between the electrophotographic photosensitive member 1 and the transfer device 6 from a transfer medium feeding portion (not shown) in synchronization with the rotation of the electrophotographic photosensitive member 1.

The transfer medium 7 to which the toner image has been transferred is separated from the surface of the electrophotographic photosensitive member 1 and introduced to a fixing device 8 for fixing the toner image, thus being ejected as a copied article (copy).

The surface of the electrophotographic photosensitive member 1 from which the toner image has been transferred to the transfer medium is cleaned with a cleaning device 9 to remove therefrom the toner or the like remaining after transfer. Then, the surface of the electrophotographic photosensitive member 1 is pre-exposed to pre-exposure light (not shown) from a pre-exposure device (not shown) to remove static electricity before being repeatedly used for forming images.

The charging device 3 may be a scorotron or a corotoron charger using corona discharge, or a contact-type charger including a charging member in the form of a roller, a blade, or a brush.

In an embodiment of the present disclosure, the electrophotographic photosensitive member 1 and at least one selected from among the charging device 3, the developing device 5, and the cleaning device 9 are integrated into a cartridge. The process cartridge may be removably mounted to the body of an electrophotographic apparatus. For example, at least one selected from among the charging device 3, the developing device 5, the transfer device 6, and the cleaning device 9 is integrated with the electrophotographic photosensitive member 1 into a cartridge. The cartridge may be guided by a guide as rails 11 and 12, thus being used as a process cartridge 10 removable from the body of the electrophotographic apparatus.

EXAMPLES

The subject matter of the present disclosure will be further described in detail with reference to Examples and Comparative Examples, but it is not limited to the Examples. The term "part(s)" used hereinafter refers to "part(s) by mass". The boiling points of the solvents used in the Examples and Comparative Examples are shown in Table 1.

TABLE 1

| Solvent | Boiling point |
| --- | --- |
| N,N-dimethylacetamide | 166° C. |
| N,N-dimethylformamide | 153° C. |
| N,N-diethylformamide | 177° C. |
| Dimethyl sulfoxide | 189° C. |
| Methyl acetate | 58° C. |
| Ethyl acetate | 77° C. |
| Propyl acetate | 101° C. |
| Isopropyl acetate | 89° C. |
| Methyl hexanoate | 150° C. |
| Ethyl hexanoate | 167° C. |
| Methyl heptanoate | 172° C. |
| Ethyl heptanoate | 188° C. |
| Methyl n-octanoate | 194° C. |
| Ethyl n-octanoate | 208° C. |
| Cyclohexanone | 156° C. |
| Acetone | 56° C. |
| Toluene | 111° C. |
| o-Xylene | 144° C. |
| m-Xylene | 139° C. |
| p-Xylene | 138° C. |
| Cumene | 152° C. |
| Mesitylene | 165° C. |
| p-Cymene | 177° C. |
| 1,2,4,5-Tetramethylbenzene | 197° C. |
| tert-Butylbenzene | 168° C. |
| Chlorobenzene | 132° C. |
| o-Dichlorobenzene | 180° C. |
| Octane | 126° C. |
| Cyclohexane | 81° C. |
| Methylcyclohexane | 101° C. |
| Ethylcyclohexane | 132° C. |
| Cycloheptane | 118° C. |
| Cyclooctane | 149° C. |
| Methylal | 42° C. |
| Hexane | 69° C. |

The materials used for producing carboxylic acid anhydrides and the resulting carboxylic acid anhydrides were identified by nuclear magnetic resonance spectroscopy (NMR). Also, carboxylic imides were identified by nuclear magnetic resonance spectroscopy (NMR) and mass spectrometry. The NMR and mass spectrometry were performed as below.

Nuclear Magnetic Resonance Spectroscopy (NMR)

The structure of each sample was confirmed using the $^1$H-NMR spectrum obtained in deuterated dimethyl sulfoxide with a Fourier transform nuclear magnetic resonance spectrometer (FT-NMR, AVANCE III 500 manufactured by Bruker).

Mass Spectrometry

The molecular weight of each sample was measured at an accelerating voltage of 20 kV with a mass spectrometer (MALDI-TOF MS, Ultraflex manufactured by Bruker) in Reflector mode, using fullerene $C_{60}$ as the molecular weight standard. For identification, the peak top molecular weight was used.

Example 1

Into a 1 L three-neck flask were added 100.0 g of a composition containing 1,4,5,8-naphthalenetetracarboxylic acid and 1,4,5,8-naphthalenetetracarboxylic acid dianhydride with a mass ratio of 62:38 and 300 mL of N,N-dimethylacetamide as a solvent at room temperature in a nitrogen flow. After being heated up to 120° C., the materials in the flask were subjected to a reaction with stirring at that temperature for 2 hours. The flask was cooled to 10° C., and the sample was stirred for 1 hour and then filtered to yield 85 g of 1,4,5,8-naphthalenetetracarboxylic acid dianhydride.

Example 2

The same operation as in Example 1 was performed, except that 300 mL of N,N-dimethylacetamide was replaced with the mixed solvent made up of 200 mL of N,N-dimethylacetamide and 200 mL of toluene, and that the materials were heated up to 111° C.

Examples 3 to 5

The same operation as in Example 1 was performed except that the solvent, the reaction temperature (heating temperature), and the reaction time were changed in accordance with those shown in Table 2.

Example 6

Into a 1000 mL three-neck flask were added 100.0 g of a composition containing 1,4,5,8-naphthalenetetracarboxylic acid and 1,4,5,8-naphthalenetetracarboxylic acid monoanhydride with a mass ratio of 86:14 and the solvent made up of 200 mL of N,N-dimethylacetamide and 400 mL of toluene at room temperature in a nitrogen flow. After being heated up to 111° C., the materials in the flask were subjected to a reaction with stirring at that temperature for 2 hours. The flask was cooled to 10° C., and the sample was stirred for 1 hour and then filtered to yield 73 g of 1,4,5,8-naphthalenetetracarboxylic acid dianhydride.

Examples 7 to 12 and 14 to 38

The same operation as in Example 6 was performed, except that the solvent, the reaction temperature (heating temperature), and the reaction time were changed in accordance with those shown in Table 2.

Example 39

Into a 3 L three-neck flask were added 100 g of pyromellitic acid and the solvent made up of 200 mL of N,N-dimethylacetamide, 1000 mL of chlorobenzene, and 400 mL of toluene at room temperature in a nitrogen flow. After being heated up to 111° C., the materials in the flask were subjected to a reaction with stirring at that temperature for 20 hours. After the solvent was removed, the reaction product was washed by being dispersed in toluene and then filtered to yield 42 g of pyromellitic acid dianhydride.

Examples 40 to 42

The same operation as in Example 39 was performed, except that the solvent and the reaction temperature (heating temperature) were changed in accordance with those shown in Table 2.

Example 43

Into a 300 mL three-neck flask were added 10.0 g of 3,3',4,4'-biphenyltetracarboxylic acid and the solvent made up of 20 mL of N,N-dimethylacetamide, 100 mL of chlorobenzene, and 40 mL of toluene at room temperature in a nitrogen flow. After being heated up to 111° C., the materials in the flask were subjected to a reaction with stirring at that temperature for 20 hours. After the solvent was removed, the reaction product was washed by being dispersed in toluene and then filtered to yield 5.1 g of 3,3',4,4'-biphenyltetracarboxylic acid dianhydride.

Example 44

The same operation as in Example 43 was performed, except that the solvent and the reaction temperature (heating temperature) were changed in accordance with those shown in Table 2.

Example 45

Into a 300 mL three-neck flask were added 10.0 g of trimellitic acid and the solvent made up of 20 mL of N,N-dimethylacetamide, 100 mL of chlorobenzene, and 40 mL of toluene at room temperature in a nitrogen flow. After being heated up to 111° C., the materials in the flask were subjected to a reaction with stirring at that temperature for 10 hours. After the solvent was removed, the reaction product was washed by being dispersed in toluene, and thus 5.7 g of trimellitic acid anhydride was obtained.

Example 46

The same operation as in Example 45 was performed, except that the solvent and the reaction temperature (heating temperature) were changed in accordance with those shown in Table 2.

Example 47

Into a 300 mL three-neck flask were added 10.0 g of 4-methylphthalic acid and the solvent made up of 20 mL of N,N-dimethylacetamide, 100 mL of chlorobenzene, and 40 mL of toluene at room temperature in a nitrogen flow. After being heated up to 111° C., the materials in the flask were subjected to a reaction with stirring at that temperature for 10 hours. After the solvent was removed, the reaction product was washed by being dispersed in toluene, and thus 3.6 g of 4-methylphthalic acid anhydride was obtained.

Example 48

Into a 300 mL three-neck flask were added 10.0 g of 2,3-naphthalenedicarboxylic acid and the solvent made up of 20 mL of N,N-dimethylacetamide, 100 mL of chlorobenzene, and 40 mL of toluene at room temperature in a nitrogen flow. After being heated up to 111° C., the materials in the flask were subjected to a reaction with stirring at that temperature for 10 hours. After the solvent was removed, the reaction product was washed by being dispersed in toluene, and thus 4.1 g of 2,3-naphthalenedicarboxylic acid anhydride was obtained.

Comparative Examples 1 to 2

The same operation as in Example 6 was performed, except that the solvent and the reaction temperature (heating temperature) were changed in accordance with those shown in Table 2. However 1,4,5,8-naphthalenetetracarboxylic acid dianhydride was not obtained.

TABLE 2

| Example No. | Solvent(s) | Volume (mL) | Reaction temperature (° C.) | Reaction time |
|---|---|---|---|---|
| 1 | N,N-dimethylacetamide | 300 | 120 | 2 h |
| 2 | N,N-dimethylacetamide/Toluene | 200/200 | 111 | 2 h |
| 3 | N,N-dimethylacetamide/Toluene | 200/400 | 111 | 2 h |
| 4 | N,N-dimethylacetamide | 500 | 165 | 30 min |
| 5 | N,N-dimethylacetamide/p-Cymene | 250/250 | 165 | 30 min |
| 6 | N,N-dimethylacetamide/Toluene | 200/400 | 111 | 2 h |
| 7 | Dimethyl sulfoxide/Toluene | 200/400 | 111 | 2 h |
| 8 | N,N-dimethylformamide/Toluene | 200/400 | 111 | 2 h |
| 9 | N,N-diethylformamide/Toluene | 200/400 | 111 | 2 h |
| 10 | N,N-dimethylacetamide/o-Xylene | 200/400 | 120 | 2 h |
| 11 | N,N-dimethylformamide/m-Xylene | 200/400 | 120 | 2 h |
| 12 | N,N-dimethylformamide/p-Xylene | 200/400 | 120 | 2 h |
| 14 | N,N-dimethylacetamide/Cumene | 200/400 | 120 | 2 h |
| 15 | N,N-dimethylacetamide/Mesitylene | 200/400 | 120 | 2 h |
| 16 | N,N-dimethylacetamide/p-Cymene | 200/400 | 120 | 2 h |
| 17 | N,N-dimethylacetamide/1,2,4,5-Tetramethylbenzene | 200/400 | 120 | 2 h |
| 18 | N,N-dimethylacetamide/tert-Butylbenzene | 200/400 | 120 | 2 h |
| 19 | N,N-dimethylformamide/tert-Butylbenzene | 200/400 | 120 | 2 h |
| 20 | N,N-dimethylacetamide/Chlorobenzene | 200/400 | 120 | 2 h |
| 21 | N,N-dimethylformamide/Methyl acetate | 200/400 | 58 | 20 h |
| 22 | N,N-dimethylacetamide/Ethyl acetate | 200/400 | 77 | 6 h |
| 23 | N,N-dimethylacetamide/Propyl acetate | 200/400 | 101 | 4 h |
| 24 | N,N-dimethylacetamide/Isopropyl acetate | 200/400 | 89 | 5 h |
| 25 | N,N-dimethylacetamide/Methyl hexanoate | 200/400 | 120 | 2 h |
| 26 | N,N-dimethylformamide/Ethyl hexanoate | 200/400 | 120 | 2 h |
| 27 | N,N-dimethylacetamide/Methyl heptanoate | 200/400 | 120 | 2 h |
| 28 | N,N-dimethylformamide/Ethyl heptanoate | 200/400 | 120 | 2 h |
| 29 | N,N-dimethylacetamide/Octane | 200/400 | 120 | 2 h |
| 30 | N,N-dimethylacetamide/Cyclohexane | 200/400 | 81 | 9 h |
| 31 | N,N-dimethylacetamide/Methylcyclohexane | 200/400 | 110 | 4 h |
| 32 | N,N-dimethylformamide/Ethylcyclohexane | 200/400 | 120 | 3 h |
| 33 | N,N-dimethylacetamide/Cycloheptane | 200/400 | 118 | 3 h |
| 34 | N,N-dimethylformamide/Cyclooctane | 200/400 | 120 | 3 h |
| 35 | N,N-dimethylacetamide/Acetone | 200/400 | 56 | 18 h |
| 36 | Cyclohexanone | 600 | 120 | 4 h |
| 37 | Methyl n-octanoate | 600 | 140 | 5 h |
| 38 | Ethyl n-octanoate | 600 | 140 | 5 h |
| 39 | N,N-dimethylacetamide/Chlorobenzene/Toluene | 200/1000/400 | 111 | 10 h |
| 40 | N,N-dimethylacetamide/o-Dichlorobenzene/Toluene | 200/1000/400 | 111 | 10 h |
| 41 | N,N-dimethylacetamide/Chlorobenzene/o-Xylene | 200/1000/400 | 130 | 10 h |
| 42 | N,N-dimethylacetamide/o-Dichlorobenzene/o-Xylene | 200/1000/400 | 140 | 10 h |
| 43 | N,N-dimethylacetamide/Chlorobenzene/Toluene | 200/1000/400 | 111 | 10 h |
| 44 | N,N-dimethylacetamide/Chlorobenzene/o-Xylene | 200/1000/400 | 130 | 10 h |
| 45 | N,N-dimethylacetamide/Chlorobenzene/Toluene | 200/1000/400 | 111 | 10 h |
| 46 | N,N-dimethylacetamide/Chlorobenzene/o-Xylene | 200/1000/400 | 130 | 10 h |
| 47 | N,N-dimethylacetamide/Chlorobenzene/Toluene | 200/1000/400 | 111 | 10 h |
| 48 | N,N-dimethylacetamide/Chlorobenzene/Toluene | 200/1000/400 | 111 | 10 h |
| Comparative Example 1 | Methylal | 1000 | 42 | 10 h |
| Comparative Example 2 | Hexane | 1000 | 69 | 10 h |

Example 49

Into a 500 mL three-neck flask were added 5.4 g of the 1,4,5,8-naphthalenetetracarboxylic acid dianhydride produced in Example 1, 200 mL of N,N-dimethylacetamide, 2.6 g of leucinol, 2.7 g of 2-(2-aminoethylthio)ethanol at room temperature in a nitrogen flow, and the materials were stirred for 1 hour at room temperature, and the mixture was refluxed for 7 hours. After removing dimethylacetamide from the resulting blackish brown liquid by evaporation under reduced pressure, the product was dissolved in an ethyl acetate/toluene mixed solvent.

After separation by silica gel column chromatography (eluent: ethyl acetate/toluene), some fraction of the sample, containing the intended product, was concentrated. The resulting crystals were dissolved in a toluene/hexane mixed solvent and then recrystallized to yield 2.5 g of tetracarboxylic acid diimide represented by the following formula (E1):

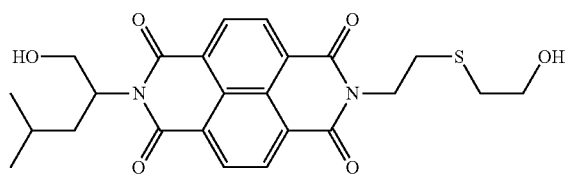

(E1)

Example 50

Into a 500 mL three-neck flask were added 5.4 g of the 1,4,5,8-naphthalenetetracarboxylic acid dianhydride produced in Example 2, 200 mL of N,N-dimethylacetamide, and 5.2 g of leucinol at room temperature in a nitrogen flow, and the materials were stirred for 1 hour at room temperature, and the mixture was refluxed for 7 hours. After dimethylacetamide was removed by evaporation under reduced pressure, the product was recrystallized in ethyl acetate to yield 5.0 g of tetracarboxylic acid diimide represented by the following formula (E2):

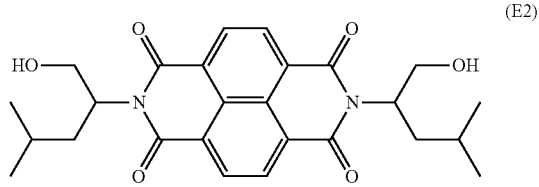 [SMILES: CC(C)CC(CO)N1C(=O)c2ccc3c4c(ccc(c24)C1=O)C(=O)N(C(CO)CC(C)C)C3=O]

(E2)

Example 51

A tetracarboxylic diimide expressed by formula (E1) was produced in the same manner as in Example 49, except that the 1,4,5,8-naphthalenetetracarboxylic acid dianhydride produced in Example 6 was used instead of the 1,4,5,8-naphthalenetetracarboxylic acid dianhydride produced in Example 1.

Example 52

A tetracarboxylic diimide expressed by formula (E1) was produced in the same manner as in Example 49, except that the 1,4,5,8-naphthalenetetracarboxylic acid dianhydride produced in Example 8 was used instead of the 1,4,5,8-naphthalenetetracarboxylic acid dianhydride produced in Example 1.

Example 53

A tetracarboxylic diimide expressed by formula (E2) was produced in the same manner as in Example 50, except that the 1,4,5,8-naphthalenetetracarboxylic acid dianhydride produced in Example 10 was used instead of the 1,4,5,8-naphthalenetetracarboxylic acid dianhydride produced in Example 2.

Example 54

A tetracarboxylic diimide expressed by formula (E2) was produced in the same manner as in Example 50, except that the 1,4,5,8-naphthalenetetracarboxylic acid dianhydride produced in Example 22 was used instead of the 1,4,5,8-naphthalenetetracarboxylic acid dianhydride produced in Example 2.

Example 55

Into a 300 mL three-neck flask were added 10.0 g of the pyromellitic acid dianhydride produced in Example 39, 100 mL of N,N-dimethylacetamide, and 11.8 g of leucinol at room temperature in a nitrogen flow, and the materials were stirred for 1 hour at room temperature, and the mixture was refluxed for 7 hours. After dimethylacetamide was removed by evaporation under reduced pressure, the product was recrystallized in a toluene/ethyl acetate mixed solvent to yield 6.7 g of tetracarboxylic acid diimide represented by the following formula (E3):

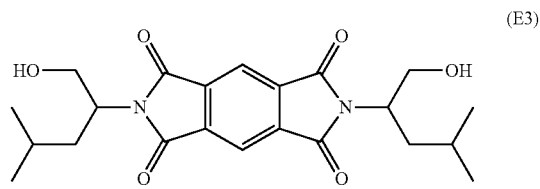 [SMILES: CC(C)CC(CO)n1c(=O)c2cc3c(=O)n(C(CO)CC(C)C)c(=O)c3cc2c1=O]

(E3)

Example 56

An aluminum cylinder (JIS-A3003 aluminum alloy) having a length of 260.5 mm and a diameter of 30 mm was used as a support member (electroconductive support member).

Then, 50 parts of oxygen-deficient tin oxide-coated titanium oxide particles (powder resistivity: 120 Ω·cm, tin oxide coverage: 40%), 40 parts of a phenol resin (product name: Plyophen J-325, manufactured by DIC, resin solid content: 60%), and 55 parts of methoxypropanol were added into a sand mill containing glass beads of 1 mm in diameter, and were dispersed in each other for 3 hours to prepare a coating liquid for forming an electroconductive layer. The average particle size of the oxygen-deficient tin oxide-coated titanium oxide particles in this coating liquid was measured with a particle size distribution analyzer CAPA 700 (manufactured by Horiba) by a centrifugal sedimentation method using tetrahydrofuran as a dispersion medium at a rotational speed of 5000 rpm. The average particle size was 0.30 µm.

This coating liquid was applied to the surface of the support member by dip coating. The resulting coating film was dried and cured by heating at 160° C. for 30 minutes. Thus, an 18 µm thick electroconductive layer was formed.

Subsequently, 1 part of the tetracarboxylic diimide represented by formula (E1) produced in Example 49, 0.5 part of a polyvinyl butyral resin (product name: BX-1, produced by Sekisui Chemical), and 0.0005 part of dioctyltin laurate were dissolved in a mixed solvent made up of 15 parts of methoxypropanol and 15 parts of tetrahydrofuran. To the resulting solution, a blocked isocyanate resin (BL 3575, produced by Sumika Bayer Urethane) was added in a proportion of 1.3 parts in terms of solid to prepare an undercoat layer-forming coating liquid. The resulting undercoat layer-forming coating liquid was applied to the surface of the electroconductive layer by dip coating. The resulting coating film was heated at 160° C. for 30 minutes so as to be cured while the solvent was removed by evaporation. Thus, a 0.8 µm thick undercoat layer was formed.

Subsequently, there was prepared crystalline hydroxygallium phthalocyanine (charge generating material) whose CuKα X-ray diffraction spectrum has peaks at Bragg angles 2θ (±0.2°) of 7.5°, 9.9°, 12.5°, 16.3°, 18.6°, 25.1° and 28.3°. Into a sand mill containing glass beads of 1 mm in diameter were added 10 parts of the crystalline hydroxytitanium phthalocyanine, 5 parts of polyvinyl butyral (product name: S-LEC BX-1, produced by Sekisui Chemical) and 250 parts of cyclohexanone. The materials were dispersed in each other in the sand mill for 2 hours. Then, 250 parts of ethyl acetate was added to the dispersion liquid to yield a coating liquid for forming a charge generating layer.

This coating liquid was applied to the surface of the undercoat layer by dip coating. The resulting coating film was dried at 95° C. for 10 minutes. Thus, a 0.17 μm thick charge generating layer was formed.

Subsequently, a coating liquid for forming a hole transport layer was prepared by dissolving the following materials in a mixed solvent made up of 40 parts of dimethoxymethane and 60 parts of o-xylene: 7.2 parts of the amine compound (hole transporting material) represented by the following formula (13):

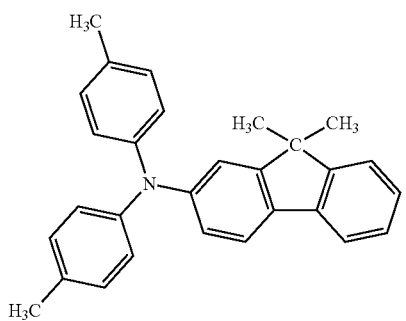

(13)

0.8 part of the amine compound (hole transporting material) represented by the following formula (14):

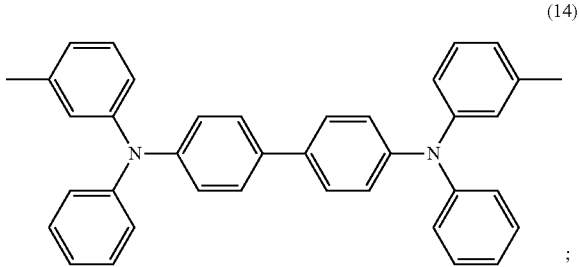

(14)

and 10 parts of polyester resin (P1) having a weight average molecular weight (Mw) of 100,000 and including the structural units represented by the following formulas (15) and (16) with a proportion of 5/5:

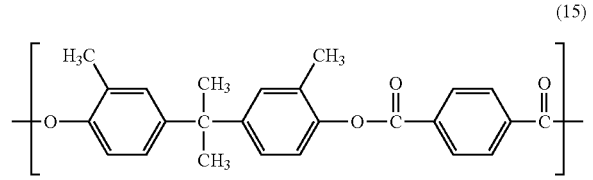

(15)

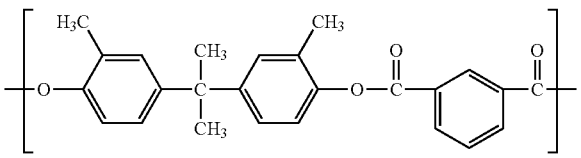

(16)

The resulting coating liquid was applied to the surface of the charge generating layer by dip coating. The resulting coating film was dried at 120° C. for 40 minutes. Thus, a 15 μm thick hole transport layer was formed.

Thus, an electrophotographic photosensitive member was produced which had the electroconductive layer, the undercoat layer, the charge generating layer and the hole transport layer on the support member.

The electrophotographic photosensitive member was installed in a printer (primary charging: roller contact DC charging, process speed: 120 mm/s, laser exposure) modified from Canon laser printer (product name: LBP-2510) under the conditions of 23° C. and 50% RH. Then, the surface potential measurement was performed before and after image output onto 15,000 sheets, and the output images were evaluated. More specifically, the evaluation was performed as below.

Ghost Examination

A cyan process cartridge of the above-mentioned laser beam printer was modified by attaching a potential probe (Model 6000B-8 manufactured by Trek Japan) to the developing position. Then, the potential at the center of the electrophotographic photosensitive member was measured with a surface electrometer (Model 344, manufactured by Trek Japan). The surface potential of the electrophotographic photosensitive member was set so that the dark portion potential (Vd) and the light portion potential (Vl) could be −600 V and −150 V respectively by controlling the amount of light to expose images.

Subsequently, the electrophotographic photosensitive member was installed in the cyan process cartridge of the laser beam printer. This process cartridge was installed in the station for the cyan process cartridge, and images were output.

First, a sheet of a white solid pattern, five sheets of a pattern for examining ghost (hereinafter referred to as ghost examination pattern), a sheet of a black solid pattern, and five sheets of the ghost examination pattern were consecutively output in that order.

Figure 2:
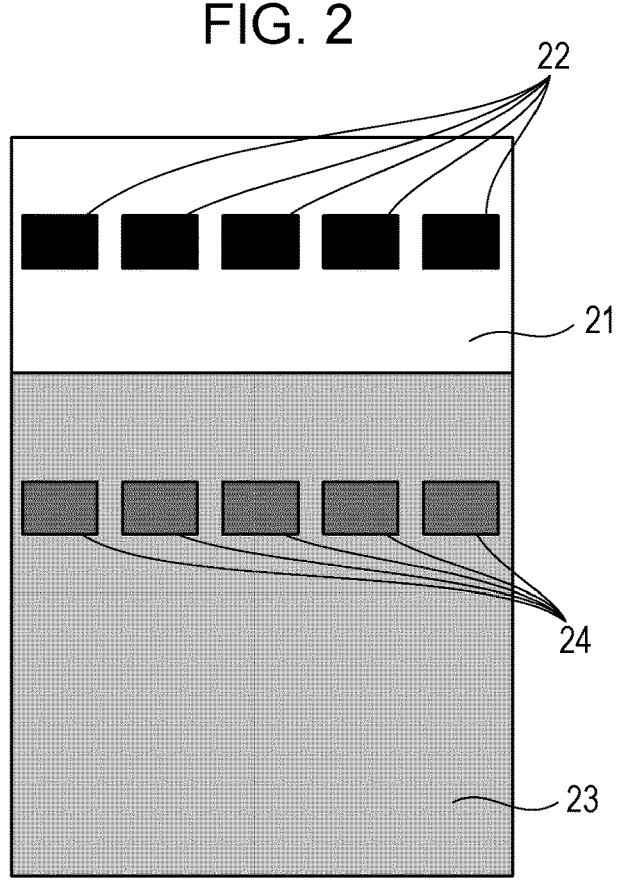
FIG. 2 is an illustrative representation of a ghost examination pattern.

The ghost examination pattern was formed as shown in FIG. 2 by printing black solid rectangles 22 in the white portion 21 of the head of the sheet and then printing a halftone dot pattern like chess knight (Shogi keima) movement as shown in FIG. 3.

For examining positive ghost, the difference in Macbeth density between the halftone dot pattern 23 like chess knight movement and the ghost portions 24 (where positive ghost could occur) was measured. More specifically, the Macbeth density difference was measured at 10 points for each sheet of the ghost examination pattern, using a spectroscopic densitometer X-Rite 504/508 (manufactured by X-Rite). This operation was performed on all the 10 sheets of the ghost examination pattern, and the average of Macbeth density differences at 100 points in total was calculated. The initial Macbeth density difference is shown in the column of Macbeth density difference (Initial) in Table 3. The Macbeth density difference after 15,000 sheet output is shown in the column of Macbeth density difference (after durability test) in Table 3. Also, the difference between the initial Macbeth density difference and the Macbeth density difference after 15,000 sheet output is shown in the column of "Macbeth density difference (after durability test)–(Initial)" in Table 3. A larger difference in Macbeth density in ghost portions suggests that a stronger positive ghost has occurred. A smaller difference in Macbeth density suggests that positive ghost has been suppressed.

Examples 57 to 61

Electrophotographic photosensitive members were produced in the same manner as in Example 56, except that the tetracarboxylic diimide produced in any one of Examples 50 to 54 was used as shown in Table 3 instead of the tetracarboxylic diimide represented by formula (E1), and the resulting samples were subjected to ghost examination in the same manner.

TABLE 3

| Example No. | Tetracarboxylic diimide | | Macbeth density difference (Initial) | Macbeth density difference (After durability test) | Macbeth density difference (After durability test) – (Initial) |
|---|---|---|---|---|---|
| | Compound | Example No. | | | |
| 56 | E1 | 49 | 0.028 | 0.037 | 0.009 |
| 57 | E2 | 50 | 0.027 | 0.036 | 0.009 |
| 58 | E1 | 51 | 0.028 | 0.038 | 0.010 |
| 59 | E1 | 52 | 0.027 | 0.038 | 0.011 |
| 60 | E2 | 53 | 0.027 | 0.036 | 0.009 |
| 61 | E2 | 54 | 0.030 | 0.039 | 0.009 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-128152, filed Jun. 25, 2015, which is hereby incorporated by reference herein in its entirety.

What is claimed is:

1. A method for producing a carboxylic acid anhydride represented by formula (2) comprising:
   a heating step performed at a temperature of 50° C. to 130° C. for heating a composition containing:
   a compound represented by formula (1), the compound being a sole acid in the composition:

   Y—(COOH)$_n$              (1)

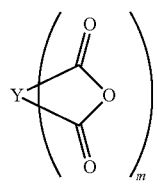 (2)

wherein in formulas (1) and (2), Y represents a divalent to hexavalent organic group, n represents an integer of 2 to 6, and m represents an integer of 1 to 3;
   (a) an aprotic polar solvent having a boiling point of 50° C. or more selected from the group consisting of methyl acetate, ethyl acetate, propyl acetate, isopropyl acetate, butyl acetate, pentyl acetate, methyl propionate, methyl valerate, ethyl valerate, methyl hexanoate, ethyl hexanoate, methyl heptanoate, ethyl heptanoate, N,N-dimethylformamide, N,N-diethylformamide, and N,N-dimethylacetamide, and dimethyl sulfoxide, and
   (b) a solvent selected from the group consisting of toluene, cyclohexane, methylcyclohexane, ethylcyclohexane, and cycloheptane.

2. The method according to claim 1, wherein a reaction time to produce the carboxylic acid anhydride is 0.1 to 4 hours.

3. The method according to claim 1, wherein Y in formulas (1) and (2) are each a group represented by formula (12):

 (12)

4. A method for producing a carboxylic imide, comprising:
   condensing a carboxylic acid anhydride represented by formula (2) produced by the method as set forth in claim 1 and an amine.

5. A method for manufacturing an electrophotographic photosensitive member including a support member, an undercoat layer over the support member, and a photosensitive layer on the undercoat layer, the method comprising:
   preparing an undercoat layer-forming coating liquid containing a carboxylic imide produced by the method as set forth in claim 4; and
   forming the undercoat layer by applying the undercoat layer-forming coating liquid to form a coating film and drying the coating film.

6. A method for producing a carboxylic acid anhydride represented by formula (5) comprising a heating step performed at a temperature of 50° C. to 130° C. for heating a composition containing:
   at least one compound selected from the group consisting of compounds represented by formula (3) and compounds represented by formula (4), the compound being a sole acid in the composition:

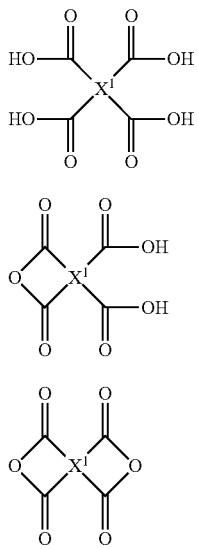

(3)
(4)
(5)

wherein in formulas (3) to (5), $X^1$ represents a residue being a tetracarboxylic acid from which four carboxy groups are removed, (a) an aprotic polar solvent having a boiling point of 50° C. or more selected from the group consisting of methyl acetate, ethyl acetate, propyl acetate, isopropyl acetate, butyl acetate, pentyl acetate, methyl propionate, methyl valerate, ethyl valerate, methyl hexanoate, ethyl hexanoate, methyl heptanoate, ethyl heptanoate, N,N-dimethylformamide, N,N-diethylformamide, and N,N-dimethylacetamide, and dimethyl sulfoxide, and (b) a solvent selected from the group consisting of toluene, cyclohexane, methylcyclohexane, ethylcyclohexane, and cycloheptane.

7. The method according to claim 6, wherein a reaction time to produce the carboxylic acid anhydride is 0.1 to 4 hours.

8. The method according to claim 6, wherein $X^1$ in formulas (3) to (5) are each a group represented by formula (12):

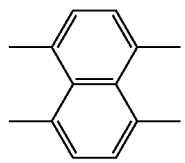

(12)

9. A method for producing a carboxylic imide, comprising:
  condensing a carboxylic acid anhydride represented by formula (5) produced by the method as set forth in claim 6 and an amine.

10. A method for manufacturing an electrophotographic photosensitive member including a support member, an undercoat layer over the support member, and a photosensitive layer on the undercoat layer, the method comprising:
  preparing an undercoat layer-forming coating liquid containing a carboxylic imide produced by the method as set forth in claim 9; and
  forming the undercoat layer by applying the undercoat layer-forming coating liquid to form a coating film and drying the coating film.

* * * * *